United States Patent [19]

Ewy et al.

[11] Patent Number: 5,435,187
[45] Date of Patent: Jul. 25, 1995

[54] END-CAP-TO-PISTON COUPLING FOR TRIAXIAL TEST APPARATUS

[75] Inventors: Russell T. Ewy; Ronald P. Steiger, both of Houston, Tex.; Rudolf J. Stankovich, Park City, Utah

[73] Assignee: Exxon Production Research Company, Houston, Tex.

[21] Appl. No.: 264,598

[22] Filed: Jun. 23, 1994

[51] Int. Cl.$^6$ ............................................. G01N 37/00
[52] U.S. Cl. .......................................... 73/856; 73/38; 73/794
[58] Field of Search ................... 73/38, 856, 859, 860, 73/794, 795, 796

[56] References Cited

U.S. PATENT DOCUMENTS

| | | |
|---|---|---|
| 2,705,418 | 4/1955 | Reichertz et al. |
| 2,737,804 | 3/1956 | Herzog et al. |
| 3,199,341 | 8/1965 | Hever, Jr. et al. |
| 3,313,151 | 4/1967 | Kaye . |
| 3,537,541 | 11/1970 | Desai et al. ............................ 181/0.5 |
| 3,975,950 | 8/1976 | Erdei ...................................... 73/795 |
| 4,380,930 | 4/1983 | Podhrasky et al. ..................... 73/594 |
| 4,487,056 | 12/1984 | Wiley ..................................... 73/38 |
| 4,502,338 | 3/1985 | Smith et al. ............................ 73/819 |
| 4,559,891 | 7/1986 | Braver et al. .......................... 73/38 |
| 4,579,003 | 1/1986 | Riley ....................................... 73/784 |
| 4,669,299 | 6/1987 | Closmann ............................... 73/38 |
| 4,679,441 | 7/1987 | Johnson et al. ........................ 73/798 |
| 4,799,382 | 1/1989 | Sprunt et al. .......................... 73/153 |
| 4,876,512 | 10/1989 | Kroeger et al. ........................ 324/376 |
| 5,025,668 | 6/1991 | Sarda et al. ............................ 73/795 |
| 5,065,421 | 11/1991 | Morineau et al. ..................... 378/208 |
| 5,265,461 | 11/1993 | Steiger et al. .......................... 73/38 |
| 5,275,063 | 1/1994 | Steiger et al. ......................... 73/865.6 |
| 5,282,384 | 2/1994 | Holbrook .............................. 73/152 |
| 5,296,145 | 3/1994 | Allington et al. ..................... 210/541 |

FOREIGN PATENT DOCUMENTS

| | | |
|---|---|---|
| 1406861 | 6/1965 | France . |
| 58-80534 | 5/1983 | Japan . |
| 2276936 | 11/1990 | Japan . |
| 5501102 | 6/1977 | U.S.S.R. . |

OTHER PUBLICATIONS

U.S. Application Ser. No. 07/913,853; filed Jul. 15, 1992; Steiger et al; co-owned with present application.
"Quantitative Determination of the Mechanical Properties of Shales", Steiger et al, SPE, 1988.
"Lateral-Deformation Gage For Rock-mechanics Testing", Schuler, 1978.

Primary Examiner—Richard E. Chilcot, Jr.
Assistant Examiner—Max H. Noori
Attorney, Agent, or Firm—Guy McClung

[57] ABSTRACT

An end-cap-to-piston coupling, with or without an integral load cell has been developed for triaxial test apparatus. One triaxial test apparatus shown has a housing, sample mounting apparatus in the housing, a load piston opening through the housing through which projects a load piston, and a load transfer coupling, with or without an integral load cell, interposed between the end cap and the load piston. In one aspect the coupling has a coupling body and a channel on one end into which the load piston is inserted to contact a shoulder of the coupling body. Another end of the coupling has a channel which receives a top end cap of a sample mounting arrangement. This channel may be sized and configured to receive a load transfer ball interposed between the coupling and the end cap or between the coupling and the piston. In one aspect a series of interchangeable top and bottom members are provided, each with a different diameter recess, to accommodate load pistons and sample end caps of different diameters.

18 Claims, 4 Drawing Sheets

Triaxial Compression
$\sigma_1 > \sigma_2 = \sigma_3$ $\sigma_{axial} > \sigma_{lateral}$ Triaxial Extension
$\sigma_1 = \sigma_2 > \sigma_3$ $\sigma_{lateral} > \sigma_{axial}$

SCREW CONNECTION

SUCTION CAP CONNECTION

RESIN POT CONNECTION

END-CAP-TO-PISTON COUPLING FOR TRIAXIAL TEST APPARATUS

BACKGROUND OF THE INVENTION

1. Field Of The Invention

This invention is related to methods and apparatuses for measuring the strength and deformation of materials under triaxial extension or compression and in one aspect to a triaxial test device including a coupling interposed between a load piston and an end cap on a test sample.

2. Description of Related Art

Triaxial compression and extension tests provide important data for the modeling of rock behavior around underground openings, in underground fluid reservoirs, around surface excavations, and beneath surface structures. With a conventional triaxial test apparatus for rock testing, a test is performed inside an enclosed housing or hydraulic cell. A confining fluid is pumped into the test cell to provide a confining pressure on a rock sample specimen. The sample is placed on a bottom end cap for support. Hydraulic pressure is applied around the sample during the test to generate an isostatic confining stress. Then an axial load is applied (e.g. by a load piston) to a top end cap to generate a deviatoric (shear) stress. During such testing, fluid leakage between the top end cap and the load piston is possible. When a sample is directly jacketed to a load piston to prevent such leakage, correct mounting and positioning of the sample and accurate measurements can be difficult. Fragile samples, such as shales and weak sandstones that are usually expensive and difficult to obtain or prepare, are often damaged in a test set up and jacketing process. In certain prior art apparatuses, load piston diameter should match sample diameter and thus a different test cell is required for each different diameter sample to be tested. The lateral stress in triaxial compression or extension tests (see FIGS. 1A and 1B) is applied by a pressurized fluid which is prevented from entering the sample by an impermeable jacket. If the axial stress is to be less than the lateral stress, as required for triaxial extension, then this fluid is not allowed to apply a pressure on the sample anywhere in the axial direction. The axial stress is applied solely by a loading piston.

Strengths and deformations are usually measured by subjecting a right circular cylinder test sample to triaxial compression conditions. As illustrated in FIG. 1A, triaxial compression is defined as a state in which two of the three principal compressive stresses are less than the third. Triaxial extension, illustrated in FIG. 1B, is a state in which two of the three principal compressive stresses are greater than the third. All stresses are still compressive, however. In contrast to metals, there is evidence that the strength of geologic materials is different under triaxial extension than under triaxial compression. It is important to know the strength under both conditions because they are the two extreme compressive stress states that can occur. Around a wellbore, for example, the stress state can lie anywhere between triaxial compression and triaxial extension. If both strengths are known, then a more accurate extrapolation of laboratory measured strengths to downhole conditions is possible.

FIG. 2 illustrates one prior art triaxial test technique which allows triaxial extension to be performed. The sample is directly jacketed to the load piston. The sample may be glued to the piston. With these methods the test cell design is usually such that radial and axial strains are measured with strain gauges mounted on the sample which are prone to errors and localized non-representative measurements. Axial strain has sometimes been determined using a single measurement of the piston displacement outside the test cell. However, this makes it impossible to separate piston slack movement from actual sample deformation, and a single displacement measurement can be affected by tilting. For the technique illustrated in FIG. 2, axial stress is usually measured outside the test cell. This causes errors due to friction around the load piston. Also, the piston diameter should match the sample diameter, so a different test cell is required for each diameter to be tested. If this is avoided by using a tapered piston, then the confining pressure has a large effect on the true axial stress. It is often difficult to accurately compensate for this.

Methods that have been used to perform triaxial extension for soils testing are illustrated in FIGS. 3A, 3B, and 3C. Only one of these methods uses a load cell located somewhat close to the sample (FIG. 3B); however, it is not an integral part of the coupling and therefore may respond to the confining pressure as well as to the axial stress. Also, the techniques illustrated were developed for testing of soils and therefore may be limited to pressures much lower than those required for typical rock testing. The methods illustrated in FIGS. 3A and 3C allow confining fluid pressure to act downward on the top end cap, but this can be overcome by means of the rigid connection between the top end cap and the axial loading system.

In prior U.S. application Ser. Nos. 07/671,367 filed Mar. 19, 1991, now U.S. Pat. No. 5,265,461; and Ser. No. 07/913,853 filed Jul. 15, 1992 (both co-owned with this application), a triaxial test apparatus is disclosed which has a top load cell mounted on a top end cap. The load cell has a self-centering steel ball disposed partially within a recess in a cylindrical steel frame. The ball puts little or no torque on a sample to be tested and provides a relatively high stress at a center point of the frame, permitting sensitive accurate load measurement. A diaphragm strain gauge is attached in a slot in the bottom of the steel frame at a point beneath the point at which the ball contacts the frame. A load piston contacts the ball to impart a load through the top end cap to a sample. A plastic cap fits snugly over the frame and has a hole in its top through which the ball protrudes. The cap prevents the ball from coming out of the frame. A typical conventional diaphragm gauge (e.g. those provided by Micromeasurements Co.) may be used. Such gauges are accurate to about 2 to 10 psi in a load range of about 6000 to 8000 psi. The gauge's range can be increased to about 15,000 by changing the thickness of the cubical frame around the slot (e.g. from 0.1 inch to 0.15 inch) and/or by using a diaphragm gauge with a higher range capability. Wiring extends from the strain gauge, through a test cell housing to interface with a monitoring and/or recording and/or controlling system. Use of the ball deals with problems associated with matching load piston and sample diameters; but it does not allow for triaxial extension testing.

SUMMARY OF THE PRESENT INVENTION

A coupling according to the present invention in one embodiment has a coupling body; an end cap channel for receiving a portion of an end cap mounted on a test sample in a triaxial test apparatus; a ball recess (which may be part of the end cap channel) for holding a ball above the end cap; and a load piston channel for receiving a load piston which pushes down on a shoulder of the coupling body. In one embodiment the ball recess is above a cross member of the body so the ball is contacted by the piston; in another embodiment the ball recess is below the cross member so the ball contacts the end cap, but not the piston. Load piston force is transferred through the coupling body to the ball (or through the ball to the coupling body), to the end cap, and then to the sample to be tested. The present invention also discloses triaxial test apparatus which includes such a coupling and such a coupling which does not include the ball. In one aspect a load cell is disposed in the body member.

In one embodiment such triaxial test apparatus includes a sealing device between the load piston and the load piston channel in the coupling and another sealing device between the end cap and the end cap channel (e.g. O-rings or Polypak (TM) seals) in the coupling. In one aspect a load gauge is mounted within a gauge recess in the coupling body shoulder. In other embodiments such a gauge is mounted on the coupling. Confining pressure (pressure due to pressurized fluid that applies lateral stress) does not act downward on the sample from above or upward on the sample from below. The confining pressure is prevented from pushing down on the top end cap by the coupling which is sealed against both the load piston and the top end cap. The gauge gives a direct measure of the axial stress acting on the sample.

Different diameter samples may be tested by using different couplings that correspond to the sample diameter. Because the sample can be sealed to both the top and bottom end caps before final assembly into the apparatus, accurate strain-measuring devices may be easily mounted on the sample. Also, because the sample assembly is set up and mounted outside the triaxial test cell there is little risk of damaging fragile samples in the process.

Preferably, test apparatus according to this invention uses a self-centering steel ball to transfer the load as described in the two previously-mentioned co-owned applications. In certain embodiments, a diaphragm gauge is mounted on the bottom of a slot which is directly under the center of the load piston and directly over the ball contact point. The deformation of the gauge measures the axial load on the top end cap, and therefore on the sample. The load range of the coupling/load cell can be varied by changing the thickness of a membrane between the ball and the gauge and/or changing the dimensions of the gauge slot. The positions of the ball and diaphragm gauge can be reversed in certain embodiments of the coupling design, producing a large confining pressure effect on the gauge in those embodiments in which the load piston is not the same diameter as the sample end cap. The coupling (which can also act as a load cell) may be made of any suitable material, such as (but not limited to) stainless steel or titanium. In certain embodiments, to ease entry of the load piston and the top end cap into the coupling, the entry points have a tapered lip, as do the ends of the load piston and the top end cap.

In one test apparatus according to this invention, strains in the axial direction are measured either by four independent linear variable differential transformers (LVDT's) or four independent cantilever strain gauges. Radial strains are measured by two pairs of cantilever strain gauges oriented 90° to each other. Radial strains can also be measured using a circumferential transverse strain measuring device. Sample pore pressures are measured using a miniature pore pressure transducer located inside a bottom end cap.

In one aspect of this invention, the sample is first jacketed to top and bottom end caps. Axial and radial strain transducers are then mounted. The assembly from the top end cap down through the base plate is then raised up into a triaxial test cell and the top end cap enters the coupling which is installed on a load piston. Confining pressure (lateral stress) and axial stress are independently applied at any desired value. In one method both confining pressure and axial stress are increased equally, and then the axial stress is reduced to cause failure under triaxial extension. Failure under triaxial extension can also be induced by increasing the confining pressure with a constant axial stress. A triaxial compression stress state can be applied (axial stress greater than lateral stress) if desired because the axial stress and lateral stress are completely independent.

It is, therefore, an object of at least certain preferred embodiments of the present invention to provide:

New, useful, unique, efficient, nonobvious triaxial test devices and methods and load transfer couplings for use therewith;

Such couplings which sealingly receive a portion of a load member such as a load piston and a portion of a sample mounting member such as a top end cap;

A series of such couplings with different replaceable upper and lower recesses to accommodate a variety of pistons and/or a variety of sample mounting members, e.g. end caps and/or pistons of different diameters.

Such couplings which have an inner space for disposition therein of a load transfer ball; and Such couplings with a load gauge.

Certain embodiments of this invention are not limited to any particular individual feature disclosed here, but include combinations of them distinguished from the prior art in their structures and functions. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention should be read to include any legally equivalent devices or methods which do not depart from the spirit and scope of the present invention.

The present invention recognizes and addresses the previously-mentioned problems and provides a solution to those problems in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of embodiments of the invention briefly summarized above may be had by references to the embodiments which are shown in the drawings which form a part of this specification, These drawings illustrate certain preferred embodiments and are not to be used to improperly limit the scope of the invention which may have other equally effective or legally equivalent embodiments.

DESCRIPTION OF EMBODIMENTS PREFERRED AT THE TIME OF FILING FOR THIS PATENT

Figure 1A:
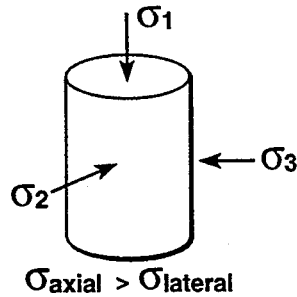
FIG. 1A illustrates triaxial compression.
Figure 1B:
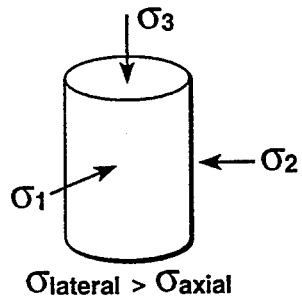
FIG. 1B illustrates triaxial extension.
Figure 2:
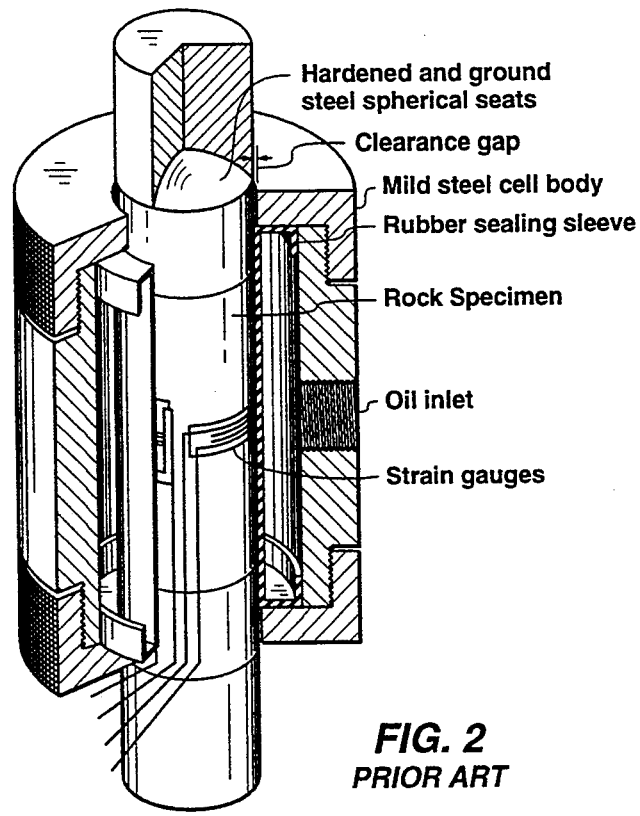
FIG. 2 is a perspective view in cross-section of a prior art triaxial test device.
Figure 3A:
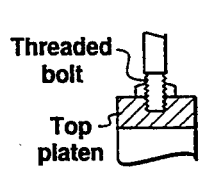
FIG. 3A is a side cross sectional view of a prior art triaxial test device.
Figure 3B:
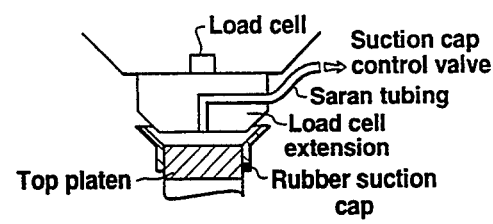
FIG. 3B is a side cross sectional view of a prior art triaxial test device.
Figure 3C:
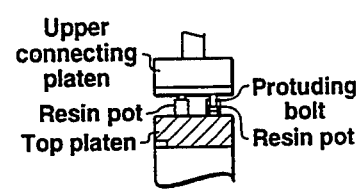
FIG. 3C is a side cross sectional view of a prior art triaxial test device.
Figure 4:
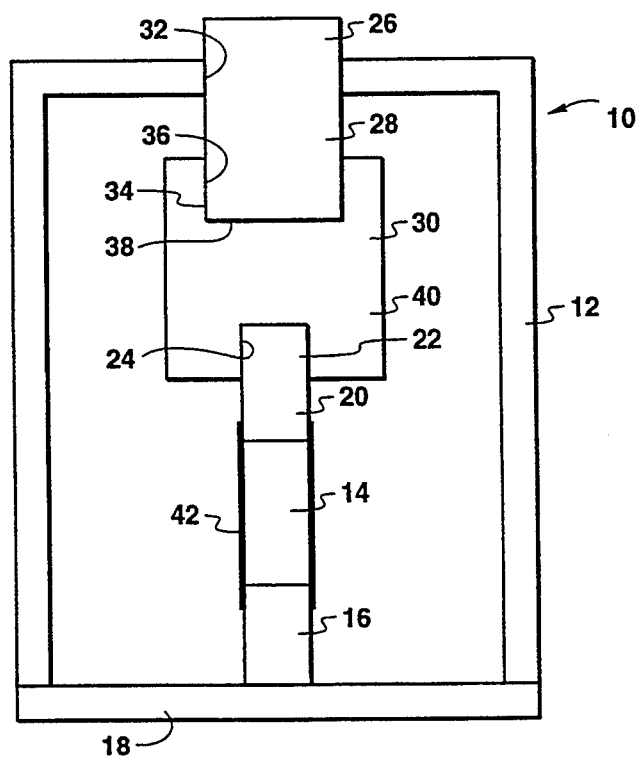
FIG. 4 is a schematic view of a device according to the present invention.

Referring now to FIG. 4, a triaxial test apparatus 10 according to the present invention has a housing 12 with a sample 14 mounted to a bottom end cap 16 which is connected to a bottom base plate 18 of the housing 12. A top end cap 20 has a top end 22 which projects into an end cap channel 24 of a coupling 30 according to the present invention. A load piston 26 interconnected with appropriate loading and control apparatus and devices (not shown) has a portion 28 which projects through an opening 32 and an end 34 which projects into a piston channel 36 in the coupling 30 to contact a body shoulder 38 of a body 40 of the coupling 30. A sample jacket 42 encompasses the sample 14. A load applied by the load piston 26 is transferred through the body shoulder 38, to and through the top end cap 20, and thence to the sample 14.

Figure 5:
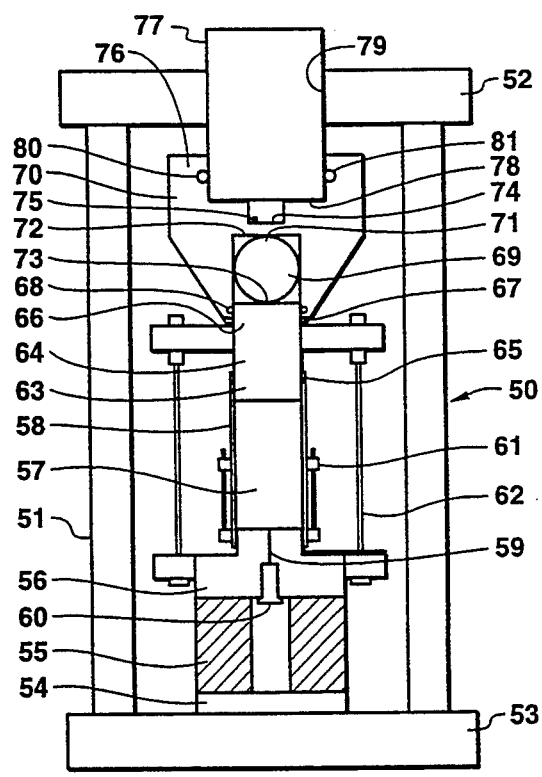
FIG. 5 is a schematic view of a device according to the present invention.

A triaxial test apparatus 50 shown in FIG. 5 has a housing 51 with a top 52 and a bottom base plate 53. An auxiliary load cell 54 is rigidly connected (e.g. by glue or bolts) to an upper surface of the bottom base plate 53 and is rigidly connected to a mount member 55 which is rigidly connected to a bottom end cap 56. A sample 57 is mounted to the bottom end cap 56 and has a sample jacket 58 around it.

A pore pressure channel 59 extends from the sample 57 to a pore pressure transducer 60. Wiring (not shown) extends from the pore pressure transducer 60 to the exterior of the base plate 53 to appropriate monitoring-/control devices. Radial strain transducers 61 respond to radial strain on the sample 57 and axial strain transducers 62 respond to axial strain on the sample 57. Appropriate wiring, conduits, connections, etc. (not shown) connect the transducers to appropriate monitor/control devices (not shown).

A portion 63 of a top end cap 64 extends into the sample jacket 58 and is clamped therein by a jacket clamp 65. An end portion 66 of the top end cap 64 is sealingly held in an end cap recess or channel 67 in a coupling 70 according to the present invention. A seal 68 is disposed between the end cap portion 66 and the inner surface of the end cap channel 67. A load centering and transferring ball 69 is disposed in the end cap channel 67 with a top portion 71 contacting an interior surface 72 of the coupling 70 and a bottom portion 73 contacting the top of the end cap 64. A load cell gauge 74 is mounted and secured in a load cell recess 75 in a body 76 of the coupling 70. (The load cell gauge may be disposed for contact by a load piston as it contacts the body.) The load piston 77 extends through an opening 79 in the top of the housing 52. A seal 80 is disposed between the load piston 77 and an inner surface of a piston channel 81 in the body 76 into which an end of the piston extends. A load from the load piston 77 is transferred to the shoulder 78, to the ball 69, to the end cap 64, and thence to the sample 57.

Figure 6:
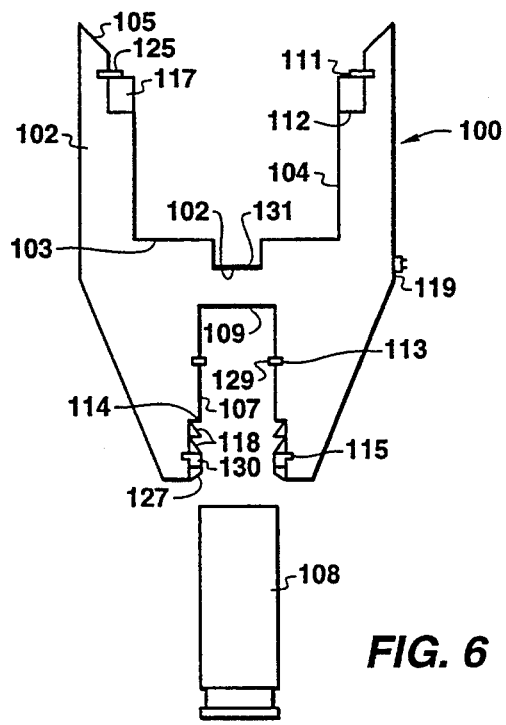
FIG. 6 is a side cross sectional view of a coupling according to the present invention.
Figure 7:
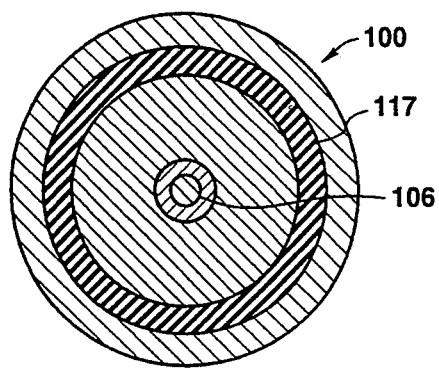
FIG. 7 is a top view of the coupling of FIG. 6.
Figure 8:
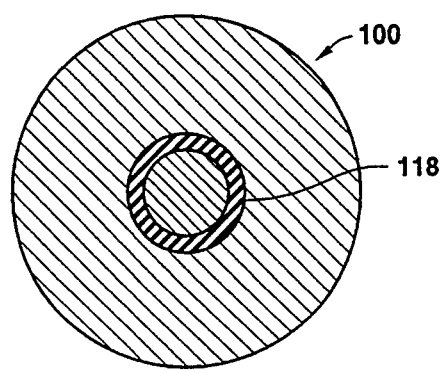
FIG. 8 is a bottom view of the coupling of FIG. 6.

A coupling 100, shown in FIG. 6, 7, and 8, according to the present invention, may be used in the apparatuses of FIGS. 4 and 5. The coupling 100 has a body 102 with an inner shoulder 103 for contact by a load piston or other load-applying member. The piston is received in a piston channel 104 which has a tapered lip 105 for ease of entry. A load cell gauge 106 (shown by a thin line in FIG. 6) may be disposed in a load cell recess 131, the gauge with leads 123 passing through a hole 116 to a sealed lead connector 119. An end cap recess 107 receives a portion of an end cap 108 so that, when a load is applied to the coupling, an interior surface 109 of the coupling 100 is pushed against an optional ball 110 (shown in outline) which in turn is pushed against the end cap 108.

The end-cap-to-coupling interface is sealed with one or more seals 118, the topmost one of which abuts a shoulder 114 of the body 102, and the bottommost seal 118 held in place with a retaining ring 130 disposed in a recess 115 in the body 102. The piston-coupling interface is sealed with a seal 117 which is on a shoulder 112 of the body 102 and which is held in place by a retaining ring 125 in a recess 111 of the body 102. An optional ball 110 (in outline in FIG. 6) is held in place by a retaining ring 129 disposed in a recess 113 in the body 102. A tapered guide 127 (e.g. made of PTFE) secured to the body 102 facilitates entry of an end cap 108 into the coupling. The tapered guide 127 abuts the retaining ring 130.

Figure 9:
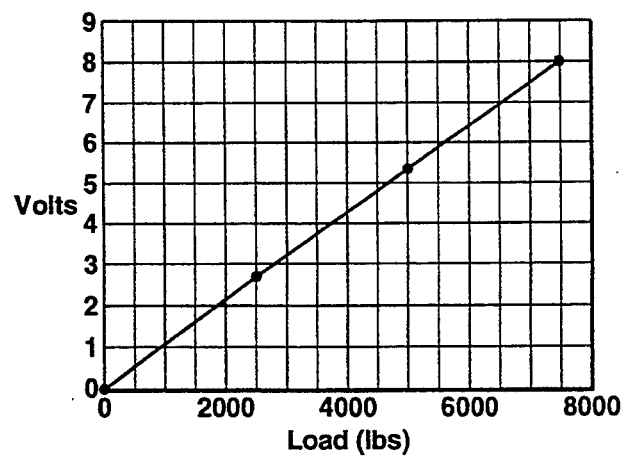
FIG. 9 is a graph showing the response of the load cell incorporated in the coupling of FIGS. 6, 7 and 8.

A coupling according to this invention as shown in FIGS. 5 and 6 with a diaphragm gauge installed in a load cell recess as shown in FIGS. 5, 6, and 7, with a load centering ball, was calibrated to 7500 lbs (approximately 17,000 p.s.i. for a 0.75 inch diameter sample) and its performance was extremely linear and repeatable, as shown in FIG. 9. The correlation coefficient for a linear fit to the data points shown is 0.9999. The load range can be varied by changing the thickness of the membrane between the ball and the gauge and/or changing the dimensions of the gauge slot. In the graph of FIG. 9 the vertical y-axis indicates gauge voltage output; i.e. the voltage response of the diaphragm gauge and the horizontal x-axis indicates the applied load in pounds.

Such coupling in use over a multi-week time period performed actual triaxial tests of shale samples, and proved to be very reliable. It's calibration was checked after this time period, and its slope of voltage vs. applied load was found to be within 0.13% of the slope shown in FIG. 9.

Figure 10A:
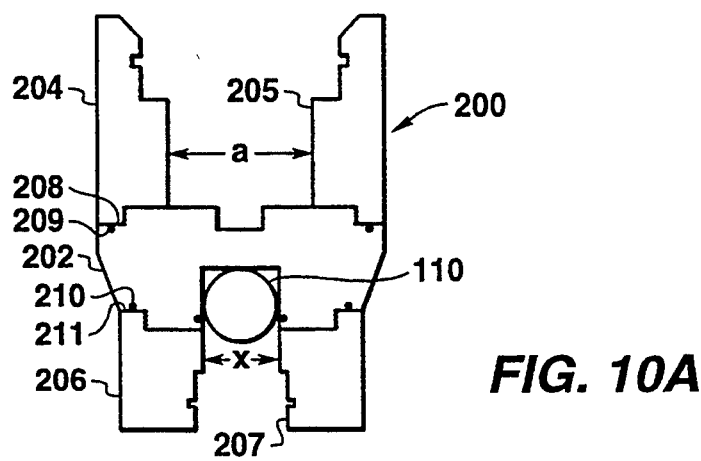
FIGS. 10A, 10B, and 10C are side cross-sectional views of couplings according to the present invention.
Figure 10B:
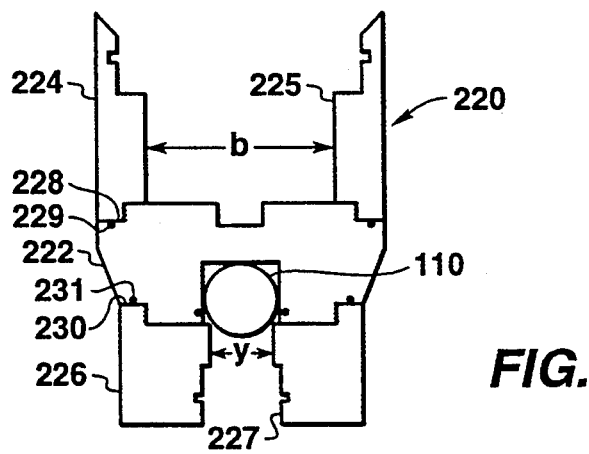
Figure 10C:
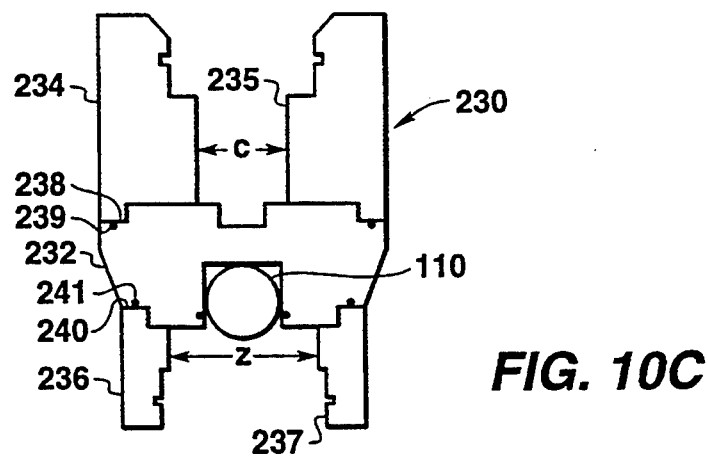

FIGS. 10A, 10B and 10C show a series of couplings according to this invention (like the previously described couplings) but with replaceable upper and/or lower members to accommodate pistons and/or end caps of different size (different diameter).

A coupling 200 shown in FIG. 10A has a main body 202, with a ball 110 therein, an upper body 204 threadedly connected to a top of the main body 202 with a seal 208 in a recess 209 in the body 202, and a lower body 206 threadedly connected to a bottom of the main body 202 with a seal 210 in a recess 211 in the body 202. The upper body 204 has a piston recess 205 that accommodates a piston of diameter a. The lower body 206 has an end cap recess 207 that accommodates an end cap of diameter x.

A coupling 220 shown in FIG. 10B has a main body 222 with a ball 110 therein, an upper body 224 threadedly connected to a top of the main body 222 with a seal 228 in a recess 229 in the body 222, and a lower body 226 threadedly connected to a bottom of the main body 222 with a seal 230 in a recess 231 in the body 222. The upper body 224 has a piston recess 225 that accommodates a piston of diameter b (greater than diameter a, FIG. 10A). The lower body 226 has an end cap recess 227 that accommodates an end cap of diameter y (smaller than diameter x, FIG. 10A).

A coupling 230 shown in FIG. 10C has a main body 232 with a ball 110 therein, an upper body 234 threadedly connected to a top of the main body 232 with a seal 238 in a recess 239 in the body 232, and a lower body 236 threadedly connected to a bottom of the main body 232 with a seal 240 in a recess 241 in the body 232. The upper body 234 has a piston recess 235 that accommodates a piston of diameter c (smaller than diameter a, FIG. 10A). The lower body 236 has an end cap recess 237 that accommodates an end cap of diameter z (larger than diameter x, FIG. 10A).

It is within the scope of this invention to secure upper and lower bodies to a main body by any suitable means; e.g., but not limited to threaded engagement, press fit, and/or glue.

In conclusion, therefore, it is seen that the present invention and the embodiments disclosed herein and those covered by the appended claims are well adapted to carry out the objectives and obtain the ends set forth. Certain changes can be made in the subject matter described, shown and claimed without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form its principles may be utilized.

What is claimed is:

1. A load coupling for transferring a load from a load piston of a triaxial test apparatus to a material sample for measuring strength of deformation of the material sample, the material sample having a top end cap thereon, the coupling comprising
    a body member having a top and a bottom,
    the body member having an end cap recess in the bottom thereof with an open end for receiving the top end cap mounted above the material sample,
    the body member having a piston recess in the top thereof for receiving a load piston of triaxial test apparatus for applying a load through the coupling and top end cap to the material sample, and
    a load cell in the body member.

2. The load coupling of claim 1 comprising also a ball recess in the body member for receiving a ball disposed between the load piston and the top end cap so that a load applied by the load piston is transferred through the ball to the top end cap.

3. The load coupling of claim 2 wherein the ball recess is below a cross member of the body member and communicates with the end cap recess, the cross member having a top and a bottom, the load piston contacting the top of the cross member, the ball contacting both the bottom of the cross member and a top of the top end cap.

4. The load coupling of claim 1 further comprising
    a first seal ring around the piston recess to seal a piston-coupling interface.

5. The load coupling of claim 4 further comprising
    first seal retention apparatus secured to the body member and abutting the first seal ring to hold it in place.

6. The load coupling of claim 1 further comprising
    a second seal ring around the end cap recess for sealing a coupling-end-cap interface.

7. The load coupling of claim 6 further comprising
    second seal retention apparatus secured to the body member and abutting the second seal ring to hold it in place.

8. The load coupling of claim 1 further comprising
    a load gauge recess in the coupling, and
    a load gauge in the load gauge recess.

9. The load coupling of claim 2 further comprising
    ball retaining apparatus disposed about the ball recess to retain the ball in the ball recess.

10. A load coupling for transferring a load from a load piston of a triaxial test apparatus to a material sample for measuring strength of deformation of the sample, the material sample having a top end cap thereon, the coupling comprising
    a body member having a top and a bottom,
    the body member having an end cap recess in the bottom thereof with an open end for receiving the top end cap mounted above the material sample,
    the body member having a piston recess in the top thereof for receiving a load piston of triaxial test apparatus for applying a load through the coupling and top end cap to the material sample, and
    end cap reception apparatus secured about the open end of the end cap recess and having an outwardly tapered lip to facilitate entry of the end cap into the end cap recess.

11. A load coupling for transferring a load from a load piston of a triaxial test apparatus to a material sample for measuring strength of deformation of the sample, the sample having a top end cap mounted thereon, the coupling comprising
    a body member having a top and a bottom,
    at least one bottom member having an end cap recess in a bottom thereof for receiving the top end cap,
    at least one top member having a piston recess in a top thereof for receiving a load piston of a triaxial test apparatus for applying a load through the coupling and top end cap to the material sample, the at least one bottom member releasably securable to the bottom of the body member, and the at least one top member releasably securable to the top of the body member.

12. The load coupling of claim 11 further comprising a ball recess in the body member for receiving a ball disposed between the load piston and the top end cap so that a load applied by the load piston is transferred through the ball to the top end cap.

13. The load coupling of claim 11 further comprising the at least one bottom member comprising a plurality of interchangeable bottom members, each with a different size end cap recess, each separately releasably securable to the body member.

14. The load coupling of claim 11 further comprising the at least one top member comprising a plurality of interchangeable top members, each with a different size piston recess, each separately releasably securable to the body member.

15. The load coupling of claim 11 further comprising a load cell in the body member.

16. The load coupling of claim 11 further comprising seal means for sealing an interface between the body member and a bottom member releasably secured to the body member.

17. The load coupling of claim 11 further comprising seal means for sealing an interface between the body member and a top member releasably secured to the body member.

18. A load coupling for transferring a load from a load piston of a triaxial test apparatus to a material sample for measuring strength of deformation of the sample, the sample having a top end cap mounted thereon, the coupling comprising a body member having a top and a bottom, a load cell in the body member, a plurality of bottom members each having an end cap recess in a bottom thereof for receiving a top end cap, each end cap recess of different size, the plurality of bottom members for accommodating end caps of different size, a plurality of top members each having a piston recess in a top thereof for receiving a load piston of a triaxial test apparatus for applying a load through the coupling and top end cap to the sample, each piston recess of different size, the plurality of top members for accommodating load pistons of different size of a triaxial test apparatus, each bottom member releasably securable to the bottom of the body member, each top member releasably securable to the top of the body member, and a ball recess in the body member for receiving a ball disposed between the load piston and the top end cap so that a load applied by the load piston is transferred through the ball to the top end cap.

* * * * *